United States Patent [19]

Wurster et al.

[11] Patent Number: 4,771,787
[45] Date of Patent: Sep. 20, 1988

[54] ULTRASONIC SCANNER AND SHOCK WAVE GENERATOR

[75] Inventors: Helmut Wurster, Oberderdingen; Werner Krauss, Maulbronn, both of Fed. Rep. of Germany

[73] Assignee: Richard Wolf GMBH, Knittlingen, Fed. Rep. of Germany

[21] Appl. No.: 940,445

[22] Filed: Dec. 11, 1986

[30] Foreign Application Priority Data

Dec. 12, 1985 [DE] Fed. Rep. of Germany ....... 3543867

[51] Int. Cl.$^4$ .............................................. A61B 10/00
[52] U.S. Cl. ............................ 128/660.03; 128/24 A; 128/328
[58] Field of Search ...................... 128/660, 24 A, 328, 128/804, 303 R

[56] References Cited

U.S. PATENT DOCUMENTS

| | | | |
|---|---|---|---|
| 3,237,623 | 3/1966 | Gordon | 128/24 |
| 3,338,235 | 8/1967 | Gordon | 128/24 |
| 3,942,531 | 3/1976 | Hoff et al. | 128/328 |
| 4,478,083 | 10/1984 | Hassler et al. | 128/660 X |
| 4,484,569 | 11/1984 | Driller et al. | 128/660 |
| 4,526,168 | 7/1985 | Hassler et al. | 128/303 R |
| 4,541,436 | 9/1985 | Hassler et al. | 128/660 |
| 4,545,385 | 10/1985 | Pirschel | 128/660 |
| 4,586,512 | 5/1986 | Dohuu et al. | 128/660 |
| 4,617,931 | 10/1986 | Dory | 128/328 |
| 4,620,545 | 11/1986 | Sheve et al. | 128/328 |
| 4,620,546 | 11/1986 | Aida et al. | 128/660 |
| 4,658,828 | 4/1987 | Dory | 128/399 X |
| 4,669,483 | 6/1987 | Hepp et al. | 128/660 |
| 4,671,292 | 6/1987 | Matzuk | 128/660 |

FOREIGN PATENT DOCUMENTS

| | | | |
|---|---|---|---|
| 2718847 | 11/1978 | Fed. Rep. of Germany | 128/24 A |
| 2722252 | 12/1978 | Fed. Rep. of Germany | 128/24 A |
| 2826828 | 7/1979 | Fed. Rep. of Germany | 128/24 A |
| 2913251 | 4/1981 | Fed. Rep. of Germany | 128/24 A |
| 3122056 | 12/1982 | Fed. Rep. of Germany | 128/328 |
| 3220751 | 12/1983 | Fed. Rep. of Germany | 128/24 A |
| 654673 | 12/1935 | Fed. Rep. of Germany | 128/24 A |
| 2140693 | 12/1984 | United Kingdom | 128/24 A |
| 0148653 | 7/1985 | United Kingdom | 128/24 A |

OTHER PUBLICATIONS

Breidenthal, R. E. et al., "Apparatus for Non-Invasive Fragmentation of Renal Calculi", Intnl. Publ. No. WO/85/03631 (PCT).

"Therapeutic Ultrasound In The Production Of Ocular Lesions", by D. Jackson Coleman, M.D., Frederic L. Lizzi, Eng. Sc.D., and Frederick A. Jakobiec, M.D., pp. 185-192 of American Journal of Ophthalmology, 86:185-192, 1978.

Primary Examiner—Francis J. Jaworski
Attorney, Agent, or Firm—Willian Brinks Olds Hofer Gilson & Lione

[57] ABSTRACT

A device for spatial location and destruction of concretions in bodily cavities by application of pulsed ultrasonic shock waves generated by a shock wave transducer focussed on the concretion in question, the shock waves being transmitted to the patient by a coupling fluid. This transducer may also be operated under reduced power if appropriate during the locating operation, as an A-scanner, according to the pulse echo mode. A B-section image of the bodily tissue traversed by the ultrasonic field is generated on a monitor by means of at least one B-scanner, so that the concretion present in the section image may be placed in coincidence with a target mark present on the monitor and indicating the position of the transducer focus by a relative displacment between the patient and the device, and the shock wave transducer may thereafter be placed in operation under corresponding high power for destruction of the concretion. A support carrying the B-scanner is displaceable with respect to the symmetry axis of the shock wave transducer during the locating operation, so that it is possible to have a plurality of different section images and thus a high degree of spatial resolution of the section scanned during the locating operation.

16 Claims, 6 Drawing Sheets

ULTRASONIC SCANNER AND SHOCK WAVE GENERATOR

BACKGROUND OF THE INVENTION

1. Field of the Invention

The invention relates to a device for spatial location and destruction of concretions in bodily cavities by application of ultrasonic shock waves which are generated in pulsed manner by a focussing shockwave transducer having its focus adjustable on the concretion in question. The transducer may, if applicable, be operated at reduced power according to the pulse echo principle as an A-scanner during the locating operation, whereas it is possible by means of at least one B-scanner to generate a B-section picture of the body tissue traversed by the ultrasonic field of a monitor, so that by means of a relative displacement between the patient and the device, the concretion depicted in the section picture may be placed in coincidence with a target mark present on the monitor and indicating the position of the transducer focus, and the shock wave transducer may subsequently be placed in operation for the purpose of destroying the concretion with the sonic pressure waves generated during the locating and destruction operations being transmitted to the patient's body via a coupling fluid.

2. Description of the Prior Art

Devices of this kind have proved themselves in the location and destruction of concretions, such as kidney, bladder and gall stones, primarily because as compared to surgical intervention, their application is less dangerous to the patient in view of the contactless destruction of the concretion in question. Difference in the function and application of the known devices derive in essence from the nature of the shock wave generation.

Various arrangements are known for providing the required coupling between a shock wave transducer and the patient. Examples are disclosed in U.S. Pat. No. 4,526,168, whose disclosure is incorporated by reference thereto and which was based on German application No. 3119295; in U.S. Pat. No. 3,237,623; in German applications Nos. 2913251 and 3220751; and in copending U.S. patent application Ser. No. 614,145, which was filed May 25, 1984 and is based on German application No. 3319871.

There are devices disclosed for example in U.S. Pat. No. 3,942,531 which claimed priority from German application 2351247 and German patent specifications Nos. 2718847; 2722252; 2913251; 3122056 and 3220751 in which the shock waves are generated by spark discharge at a focus of a partially eliptical focussing chamber and the other focus may be placed in coincidence with the concretion which is to be destroyed, by adjustment of the device. Relatively high striking voltages are required for spark discharges, as known, so that problems arise in the provision of suitable electrical insulation for the patient, which are costly to resolve. Furthermore, spark discharges lead to burn-off of the electrodes, so that a commensurate maintenance cost will occur.

Ultrasonic transducers will be more satisfactory in this connection, if they comprise one or more commonly, several ceramic elements and are operated by voltage in a pulsed manner, for example, in water as a coupling fluid with respect to the patient. Transducers of this nature, which are disclosed for example in U.S. patent application Ser. No. 614,145, German patent application No. 654673, the above mentioned U.S. Pat. No. 4,526,168 and U.S. Pat. No. 4,607,931, whose disclosure is incorporated by reference and claims priority from the same French application as EP specification No. 148653, are advantageous, in particular because of their durability and risk-free application. Focussing transducers may also be produced in comparatively uncomplicated manner, by mosaic-like positioning of individual transducer elements on a support in the shape of a spheroidal cap or cup, for example. On the other hand, an electronic focussing action is also possible in the case of such transducers assembled from several transducer elements, by appropriate chronologically staged actuation of the transducer elements.

A special problem arises however in these devices in connection with the location of the concretion and the alignment of the focus of the shock wave transducer on the concretion. In this connection, an adjustment under X-ray observation is not advisable in view of the patient's radiation exposure. For this reason, the method has already been adapted to generate sectional pictures of the organ or body area in question by means of B-scanners and to adjust the focus of the shock wave transducer with respect to the concretion under observation of the section pictures on monitors. If, for example, two scanners arranged at an angle of 90° with respect to each other are utilized, the concretions may be clearly depicted on the monitor in two sectioning planes and the focus may if applicable still be adjusted in another plane relative to the concretion by displacement of the shock wave transducer.

It will frequently be sufficient however if the position of the focus is indicated on the monitor by means of a target mark, and if the concretion displayed on the monitor by means of the sectional pictures is placed in coincidence with the target mark by displacement of the device or variation of the patient's position. The shock wave transducer may furthermore also be involved in the locating operation, by allowing it to operate at comparatively low power as an A-scanner in a transceiver mode or rather according to the pulse echo principle. It is possible upon occurrence of a typical maximum of the echo signals being equally displayed on the monitor, to determine whether the transducer focus will be situated within or on the concretion.

SUMMARY OF THE INVENTION

It is an object of the invention to provide a device for locating and destroying a concretion, which simplifies the components required for the purpose of location and is thus economic, and which also allows direct optical display of the shattering operation. Furthermore, the reliability and precision of the location of concretions is to be improved.

These objects are achieved in accordance with the invention in that a device of the type referred to above is so constructed that the B-scanner is displaceable on a support by first means for moving the scanner and support with respect to the symmetry axis of the shock wave transducer or transducer means. In this connection, the support and B-scanner may be rotatable by the first means around the symmetry axis of the shock wave transducer. Additionally or alternatively the B-scanner may be axially displaceable by the first means.

An arrangement, which is structurally uncomplicated and reliable regarding the locating operation, can be obtained if the symmetry axis of the shock wave transducer and the longitudinal axis of the B-scanner coincide. This does not however prevent the B-scanner from being installed on a rim of the shock wave transducer means for example, and furthermore from being pivoted or turned along an arc with respect to the symmetry axis of the transducer.

The displaceability of the B-scanner with respect to the shock wave transducer establishes the possibility, depending on the number of scanner settings selected, of placing a plurality of sectioning planes through the corresponding section of the body and thereby establishing a comparatively high degree of spatial resolution of the section in which the concretion is presumed to be located. If the concretion is visible in a sectioning plane on the monitor and has been placed in coincidence with the target mark denoting the transducer focus by relative displacement between the patient and the shock wave transducer, at least one plane or spatial coordinate is determined for the position of the focus with respect to the concretion.

After displacing the B-scanner to another position, for example by turning it through 90°, the position of the concretion in another sectioning plane is sought and found in the manner referred to in the foregoing, so that another coordinate is established, which will normally be sufficient to establish, with some certainty, that the transducer focus and the concretion have the same position or that the concretion is at least situated on the symmetry axis of the transducer. The transducer also may be axially displaced in this case until its focus is situated on the concretion. To this end, the transducer will operate as an A-scanner. Following this, the transducer is operated in a pulsed manner under full power to destroy the concretion.

The possibility exists moreover by means of the B-scanner, to receive a shock wave echo reflected by the concretion and to display the same on the monitor, so that the position of the focus may be constantly verified optically even during the application of the shock waves.

To this end, the control for the pulse generator operating the shock wave transducer and the B-scanner will include means for synchronising the shock wave transducer and B-scanner in such a manner that the shock wave echo signal can be received by the B-scanner. If the transducer element of the B-scanner is wobbled mechanically, the synchronization is performed in such manner that the axis of the transducer element, when switched to reception, is situated on the symmetry axis of the shock wave transducer upon arrival of the shock wave echo signal.

Further objects and advantages of the invention will be understood from the detailed description, read in conjunction with the accompanying drawings wherein preferred embodiments of the invention are illustrated.

DETAILED DESCRIPTION OF THE PREFERRED EMBODIMENTS

In all the devices illustrated in the drawings, a shock wave transducer means or transducer 1 has the shape of a spheroidal cap or cup, in which individual piezo-electric transducer elements not shown in particular are installed, and have their effective emitter surface aligned on the focus point 2. Such a focussing transducer is disclosed in the copending U.S. application Ser. No. 614,145, and consequently need not be described in particular.

Figures 1, 2:
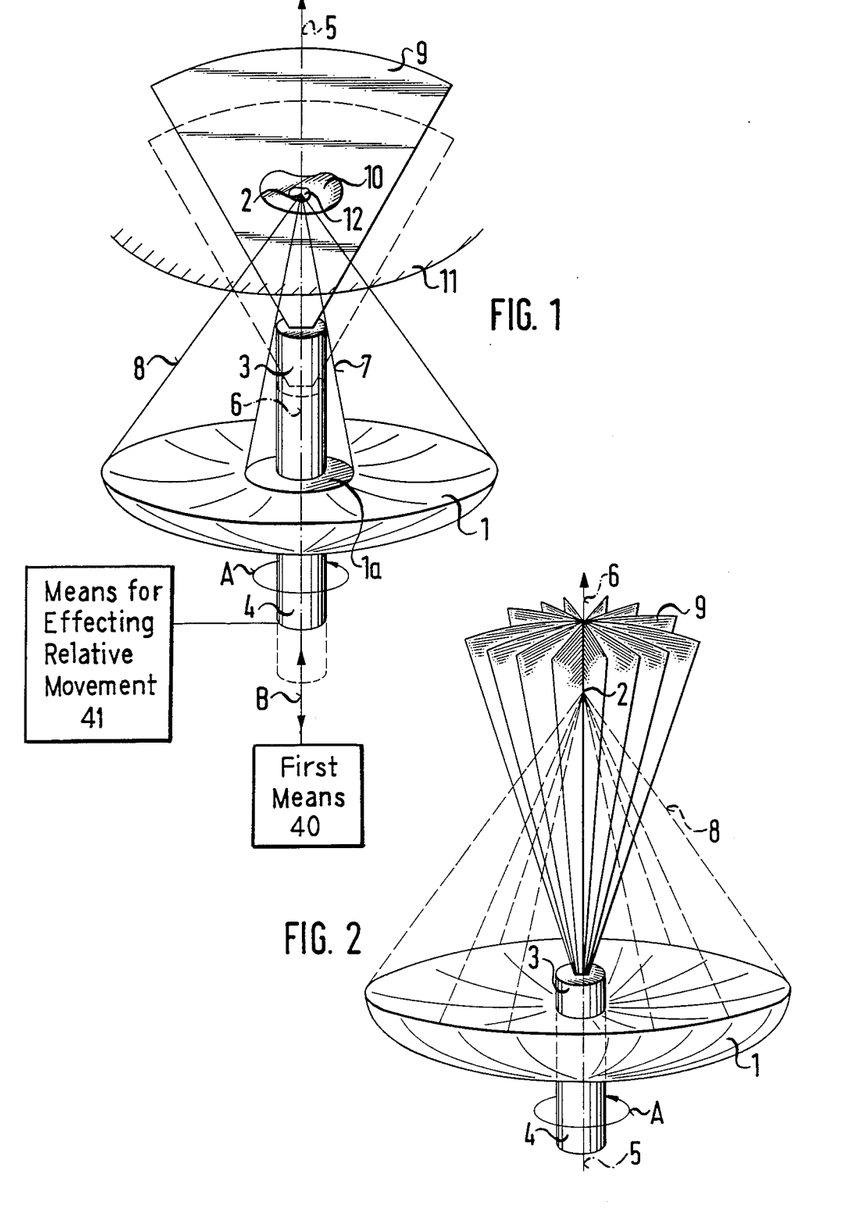
FIG. 1 is a diagrammatical perspective view of a scanner/disintegrator according to a first embodiment of the invention being focussed on a concretion.
FIG. 2 is a diagrammatical view of a second embodiment.

In the device according to FIG. 1, a B-scanner 3 is secured to the top end of a support 4 in such a manner that the longitudinal axis 5 of the scanner coincides with the symmetry axis 6 of the shock wave transducer 1. The support 4 passes through the center of the transducer 1, which lacks any transducer elements in a central area 1a so that the support 4 and the scanner 3 will be situated within a sound shadow having a peripheral shape of a cone 7, even if as in this case, the scanner of its support projects comparatively far out of the space enclosed by the spheroidal cap shape of the transducer 1.

The external outline of the shock wave field intersecting in the focus point 2 has been delineated by the cone 8. The concretion 12, which is present in a kidney 10 of the patient 11 and on which the focus or focal point 2 is already aligned in this case, should be situated in the sectioning plane 9, which is detected by the scanner 3 and lies in the plane of the drawing.

Furthermore, the device includes first means 40 for moving the support 4 and the scanner 3. In FIG. 1, the first means turns or rotates the scanner 3 in the direction of the arrow A around the symmetry axis 6. For example, the first means may turn the scanner within an angular range of 90°, so that at least two appropriately angularly staggered section images may be generated. The scanner 3 may moreover be displaced by the first means 40 in the direction of the double-headed arrow B by axial displacement of the support 4 with respect to the transducer 1, to give satisfactory adaptation of the scanner position to the patient 11. Another possible axial position of the support 4 and of the sectioning plane 9 is shown in broken lines in FIG. 1.

If, as in the embodiment of FIG. 1, the scanner 3 projects comparatively far into the conventional commutation field geometry of the transducer 1 and thus has a correspondingly smaller spacing from the concretion 12 from the start, it is advantageously possible to make use of a short-focus scanner which is commercially available and thus more advantageously priced. This advantage will not commonly be available in a device of the type illustrated in FIG. 2, in which the scanner 3 is situated actually within or immediately adjacent to the space enclosed by the cup shape of the transducer 1, and cannot be displaced axially. On the other hand, this embodiment has the advantage that only a comparatively small area need be kept free of transducer elements at the center of the transducer cup, to place the scanner and its support in a shadow.

In FIG. 2, the carrier or support 4 together with the scanner 3 is mounted by the first means (not illustrated) for rotation around the symmetry axis 6 (arrow A) at the center of the transducer. Displaying multiple sectioning planes 9 is thereby possible as in the example described in the foregoing. Seven different sectioning planes 9 are depicted and are spread over 360° in FIG. 2. It will however be possible to manage in practice with two sectioning planes staggered through an angle of 90° for example and thereby to allow accurate location of the concretion. Since the scanner will after completion of the locating operation and also during operation of the transducer 1 remain in its illustrated position and be able to generate B-images currently, a B-scanner of comparatively long focus or focal range will moreover be needed in this device on the one hand, but on the other hand an ultrasonic check via the scanner is also possible during application of the shock waves.

As for the rest, the two devices according to FIGS. 1 and 2 comply with ideal conditions for locating and destroying bodily concretions, since the transducer 1 and the B-scanner 3 are situated on the same axis 6 and since identical tissue strata are traversed for this reason by the sonic locating field as well as by the shock wave sonic field. It is consequently not normally possible to cause refractions of the wave fronts of the two sonic fields causing possible differential image defects.

If, however, such image defects or aberrations do not occur or are negligible in connection with the location, display and locus of the shock wave focus, the B-scanner may also be installed offset from the symmetry axis 6 on a marginal area of the transducer 1 and be turned by the first means with respect to the transducer around the symmetry axis 6. To this end, FIGS. 3-7 show some realizable possibilities in diagrammatical and greatly simplified manner.

Figure 3:
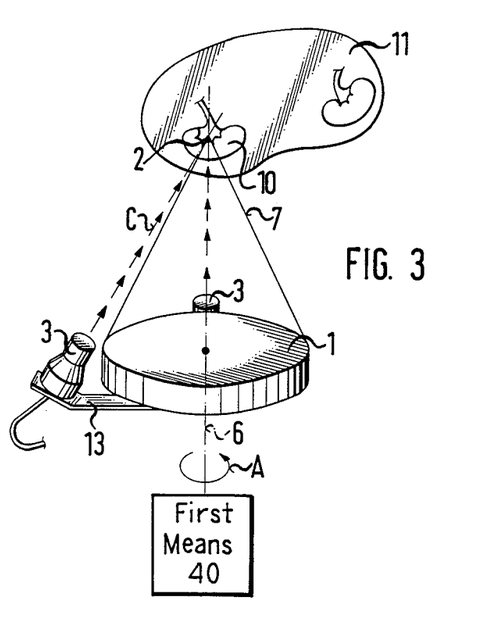
FIG. 3 is a diagrammatical view of a third embodiment.
Figure 4:
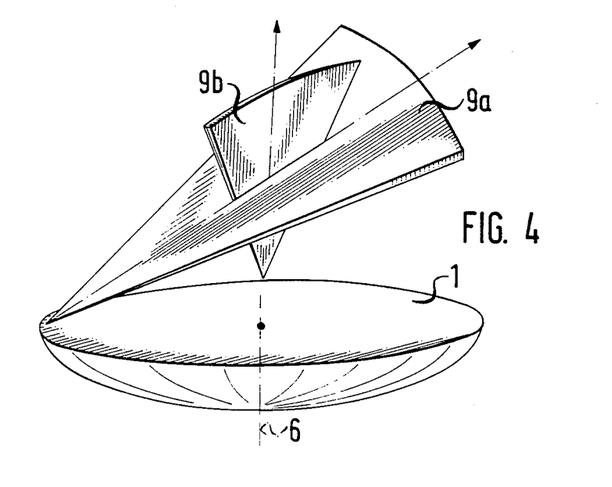
FIG. 4 is a view of two sectioning planes obtained by rotation of the scanner of FIG. 3 through 90° about the axis of the disintegrator.
Figure 5:
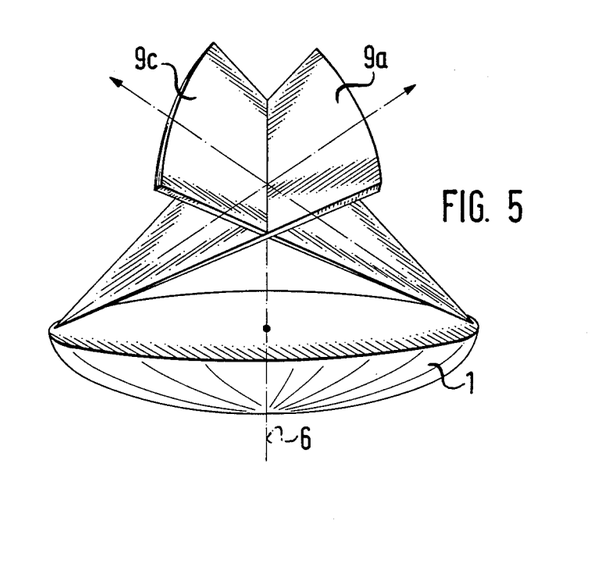
FIG. 5 is a view of two sectioning planes obtained by rotation of the scanner of FIG. 3 through 180° about the axis of the disintegrator.
Figure 6:
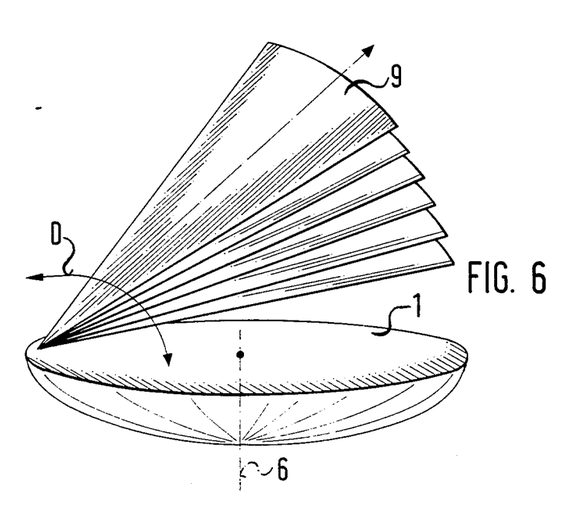
FIG. 6 is a view of a series of sectioning planes obtained by pivotal displacement of the scanner of FIG. 3.

According to FIG. 3, the scanner 3 is so secured on a support 13 that it has its axis fixedly aligned on the focal point or focus 2 of the transducer 1, as shown by the arrows C. The support may moreover be turned together with the scanner around the axis 6 by the first means 40 in the direction of the arrow A in this case, that is to say for example through 90° from the left-hand position in the drawing to the rear position, so that two different sectioning planes 9a, 9b (FIG. 4) are the result. If the scanner is povoted by the first means from the one position through 180° to another position with respect to the transducer in the corresponding manner, two sectioning planes 9a and 9c (FIG. 5) will result.

Figure 7:
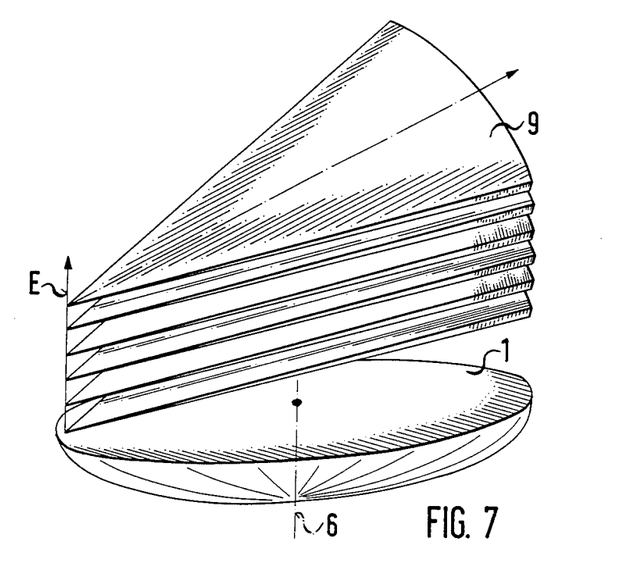
FIG. 7 is a view of a series of sectioning planes obtained by axial displacement of the scanner of FIG. 3.

The first means can have a displacement of the support and the B-scanner with respect to the transducer for the purpose of generating several section images. The displacement may be either a pivotal displacement of the support and scanner in the direction of the arrow D around a fixed point (FIG. 6) or an axial displacement in the direction of the arrow E (FIG. 7). The displacement of the sectioning planes is either offset in a fanlike manner in one case or offset in a tier-like manner in the other case.

Figure 8:
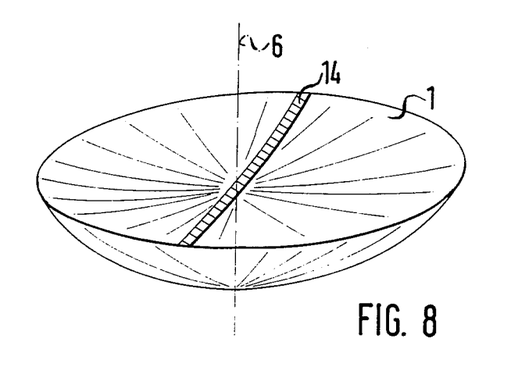
FIG. 8 is a view of a B-scanner in accordance with a fourth embodiment.
Figure 9:
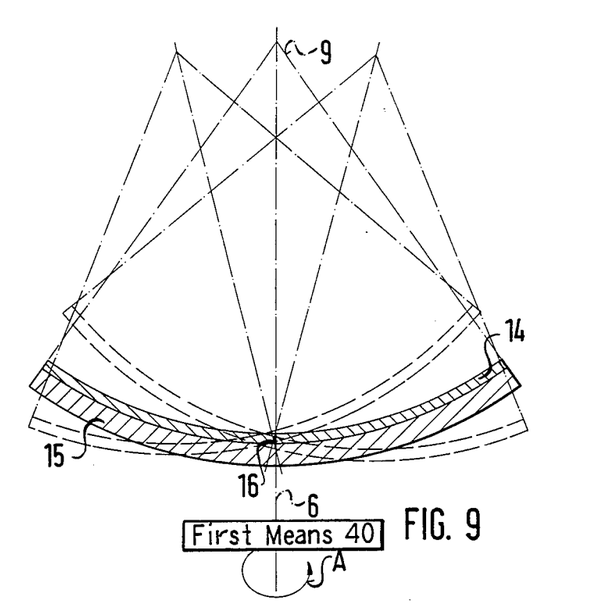
FIG. 9 is a cross-sectional view to diagrammatically illustrate a pivotal displacement of the scanner of FIG. 8.
Figure 10:
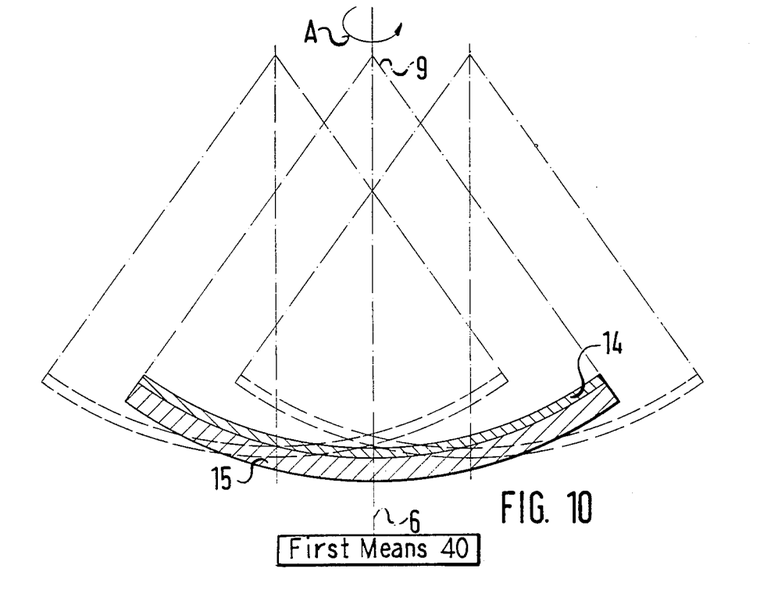
FIG. 10 is a cross-sectional view to diagrammatically illustrate the lateral displacement of the scanner of FIG. 8.

Another possibility for a particular embodiment and displacement of the B-scanner emerges from FIGS. 8-10. In this case, the B-scanner 14 is in the form of a strip comprising at least one piezo-electric transducer element. It extends in the plane of the spheroidal shock wave transducer 1 and through its center, so that in this case too, the symmetry axis 6 of the transducer coincides with the axis of the B-scanner.

The support 15 for the transducer element or transducer elements 14 may be pivoted by the first means out of the center and around a bearing point 16 with respect to the transducer 1, as can be seen in FIG. 9. Additionally or instead, the support 15 and scanner may be displaced linearly according to FIG. 10, so that several sectioning planes will be the result as denoted by dash-dotted lines in FIGS. 9 and 10. Since an unequivocal location of the concretion by means of the B-section images thus produced may well still not be possible by this method, the shock wave transducer 1 should also be rotatably arranged around the symmetry axis 6 together with the scanner 14, so that even more section images staggered by means of preset angles of rotation may be displayed in this manner.

Figure 11:
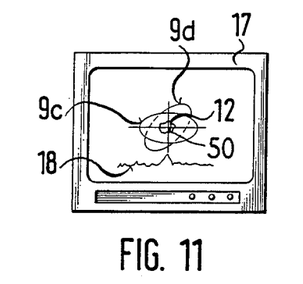
FIGS. 11 and 12 are front views of a monitor to illustrate how a concretion is located using a monitor.
Figure 12:
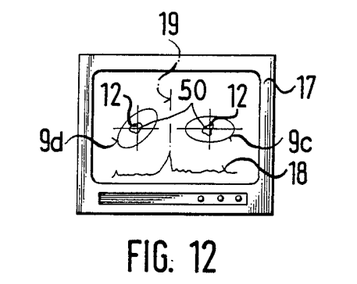

Upon locating a concretion, use is normally made of at least one monitor 17 in conjunction with target marks 50, as described in the following in connection with FIGS. 11 and 12. If it is possible to manage with two section images during the locating operation, which is commonly the case, it is possible to scribe one target mark 50 (FIG. 11) or two target marks 50 (FIG. 12) for both section kidney images 9c and 9d on the image screen of the monitor based on the fixedly predetermined geometrical correlation between the B-scanner and the shock wave transducer, for example as reticles as shown in the drawings. If the B-scanner is initially operated in the one sectioning plane and the concretion is present in the section image 9c, the display of the concretion 12 is placed in coincidence with the target mark by displacement of the patient or by displacing the device on one coordinate by means 41 for effecting relative movement (FIG. 1).

The B-scanner is then displaced to generate another section image 9d and the concretion is placed in coincidence with the same target mark 50 (FIG. 11) or with another target mark 50 (FIG. 12) decisive for this image plane. Thus, it is possible to be certain that a second coordinate is also determined in this connection and the focus of the shock wave transducer preset by means of the target mark is situated on or within the concretion and that the transducer may now be placed in operation to disintegrate the concretion.

It is, however, also possible and known that the shock wave transducer may complementarily also be utilized as an Ascanner to display a pulse echo 18 on the monitor 17 and arrange matters by displacement of the A-scanner so that it is known precisely thanks to a third coordinate, whether the transducer focus is correctly adjusted or whether the transducer still has to be displaced along this coordinate. The correct setting is reached in any case when the maximum of the echo is situated below the concretion 12 depicted, accordng to FIG. 11, or coincides with another target mark 19 as shown in FIG. 12.

If the B-scanner is axially displaceable as in the examples of embodiment according to FIGS. 1 and 7, it will be necessary to scribe a target mark on the monitor for each of the sectioning planes which are preset and may be obtained by axial displacement, in which connection it is possible to make do with a single target mark in a device as shown in FIGS. 2 and 3.

Figure 13:
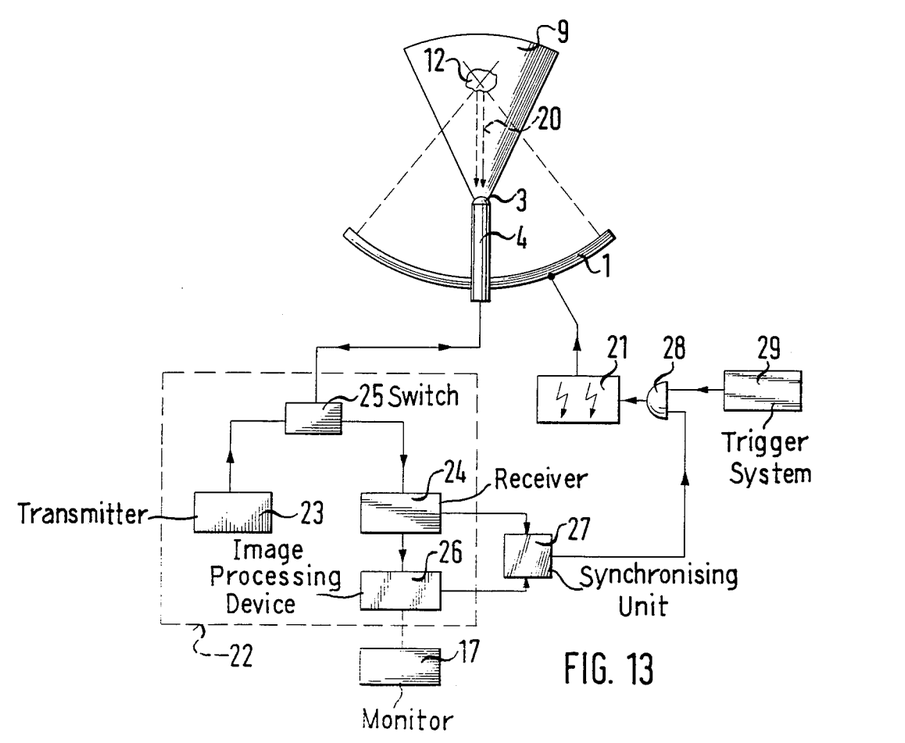
FIG. 13 is a block diagram to illustrate the circuitry for receiving and monitoring echo signals generated by the shock waves of the transducer.

It is possible by means of the device shown in FIG. 13 to receive the echo signal 20 generated by the shock wave of the transducer on the concretion 12 by means of the B-scanner 3 and to display this on the monitor 17. Apart from the normal ultrasonic B-datum, complementary information is secured thereby by superimposition of the shock wave echo. As a matter of fact, if the concretion is struck by the shock wave, a brightly shining area of the order of magnitude of the shock wave focus appears on the monitor, whereby it is then possible to determine precisely by eye, whether the concretion has been struck.

To accomplish this, a pulse generator 21 (FIG. 13) driving the shock wave transducer 1 and the scanner 3 are so synchronized in respect of the sweep motion of its transducer element of reception crystal, that the echo signal 20 may in each case be received when the axis of the transducer element, when switched to reception, is situated precisely on the symmetry axis 6 of the transducer 1.

In FIG. 13, the components appertaining to the ultrasonic B-location system are situated in a box 22 illustrated by broken lines. This system comprises a transmitter 23 and a receiver 24 which are alternately switched to the scanner 3 via a rapid-action switch 25, so that the same is periodically switched between the transmission and reception modes is each case. The echo signal 20 received by the scanner passes via the switch 25 to the receiver 24 and from the latter to an image processing device 26 which processes the signal for subsequent display on the monitor 17.

Since the reception of the shock wave echo in the case of a mechanical sweep scanner is possibly only in case of alignment of the reception crystal on the incoming echo signal, the synchronization already referred to earlier is required. For this reason, a synchronous signal is generated by the receiver 24 via a synchronizing unit or means 27 and by the image processing means 26 at the appropriate instant, and this is interlinked via an AND gate 28 with a trigger signal from a trigger system 29 controlling the pulse generator 21. This renders a triggering action on the pulse generator 21 possible in each case only if the reception conditions of the location system are present. A synchronizing action is also possible however in corresponding manner, if the B-scanner is not operated by mechanical sweep but by electrical sweep.

In conclusion, it is also pointed out that an adequate number of section images may well already be generated by means of a single scanner in view of the displaceability of the scanner support, which should not however bar another B-scanner from being placed in operation if appropriate. The additional scanner can be either fixedly or displaceably arranged with respect to the shock wave transducer. The first means for displacement of the scanner and support may be produced in optional manner and by means known per se. For example, the displacement may be performed by means of an electric motor which may transmit drive either directly or via gearing to the rotatably mounted support and if appropriate also in an axially displaceable manner.

Although various minor modifications may be suggested by those adverse in the art, it should be understood that we wish to embody within the scope of the patent granted hereon all such modifications as reasonably and properly come within the scope of our contribution to the art.

We claim:

1. A device for spatial location and destruction of a concretion in a bodily cavity of a patient, comprising a focussing shock wave transducer means for producing ultrasonic waves and having an axis of symmetry and a focus alignable with the concretion to be destroyed, a B-scanner arranged to generate a B-section image of bodily tissue of the patient traversed by the ultrasonic waves from said transducer means, a displaceable support means for mounting the B-scanner to move with the transducer means, said support means having first means to displace the B-scanner relative to the transducer means along a displacement axis that extends between the B-scanner and the focus of the transducer means, a monitor means for displaying said image, means for defining at least one target mark on said monitor means indicating the position of the transducer focus, and means for effecting relative movement between the patient and the device to bring the concretion depicted in said image into coincidence with said target mark, said shock wave transducer means adapted to generate ultrasonic shock waves in a pulsed manner to destroy the concretion at said focus.

2. A device according to claim 1, wherein said shock wave transducer means is adapted for operation at reduced power, as an A-scanner according to the pulse echo principle, for location of the concretion.

3. A device according to claim 1, wherein said first means comprises means for rotating the B-scanner around the symmetry axis of the shock wave transducer means.

4. A device according to claim 1, wherein the support means mounts the B-scanner with the symmetry axis of the shock wave transducer means and the longitudinal axis of the B-scanner coinciding.

5. A device according to claim 4, wherein the shock wave transducer means comprises individual piezoelectric transducer elements assembled into the form of a spheroidal cap, wherein the support means extends through a center of the shock wave transducer means which is unobstructed by transducer elements, and wherein the transducer elements are so arranged that the support means is situated within a sound shadow during operation of the shock wave transducer means.

6. A device according to claim 5, wherein the B-scanner on the support means projects outwards beyond the volume enclosed by the transducer cap.

7. A device according to claim 1, wherein the device further comprises pulse generator means for driving the transducer means, and means for synchronizing the pulse generator and the B-scanner so that a shock wave echo signal reflected off the concretion is received by the B-scanner.

8. A device according to claim 7, wherein the B-scanner includes a transducer element, wherein the first means comprises means for mechanically rocking the transducer element of the B-scanner, and wherein the synchronizing means comprises means for ensuring that the axis of the transducer element of the B-scanner, when switched for reception, is situated on the axis of symmetry of the shock wave transducer means at the impingement of the shock wave echo signal.

9. A device for spatial location and destruction of a concretion in a bodily cavity of a patient, comprising a focussing shock wave transducer means for producing ultrasonic waves and having an axis of symmetry and a focus alignable with the concretion to be destroyed, a B-scanner arranged to generate a B-section image of bodily tissue of the patient traversed by the ultrasonic waves from said transducer means, a displaceable support means for mounting the B-scanner to move with the transducer means, said support means having first means to displace the B-scanner relative to the transducer means along a displacement axis that extends away from the transducer means on the side of the transducer means that includes the focus such that the B-scanner is displaceable away from the transducer in a direction that includes a component parallel to the symmetry axis, a monitor means for displaying said image, means for defining at least one target mark on said monitor means indicating the position of the transducer focus, and means for effecting relative movement between the patient and the device to bring the concretion depicted in said image into coincidence with said target mark, said shock wave transducer means adapted to generate ultrasonic shock waves in a pulsed manner to destroy the concretion at said focus.

10. A device according to claim 9, wherein said shock wave transducer means is adapted for operation at reduced power, as an A-scanner according to the pulse echo principle, for location of the concretion.

11. A device according to claim 9, wherein said first means comprises means for rotating the B-scanner around the symmetry axis of the shock wave transducer means.

12. A device according to claim 9, wherein the support means mounts the B-scanner with the symmetry axis of the shock wave transducer means and the longitudinal axis of the B-scanner coinciding.

13. A device according to claim 9, wherein the shock wave transducer means comprises individual piezoelectric transducer elements assembled into the form of a spheroidal cap, wherein the support means extends through a center of the shock wave transducer means which is unobstructed by transducer elements, and wherein the transducer elements are so arranged that the support means is situated within a sound shadow during operation of the shock wave transducer means.

14. A device according to claim 13, wherein the B-scanner on the support means projects outwards beyond the volume enclosed by the transducer cap.

15. A device according to claim 9, wherein the device further comprises pulse generator means for driving the transducer means, and means for synchronizing the pulse generator and the B-scanner so that a shock wave echo signal reflected off the concretion is received by the B-scanner.

16. A device according to claim 15, wherein the B-scanner includes a transducer element, wherein the first means comprises means for mechanically rocking the transducer element of the B-scanner, and wherein the synchronizing means comprises means for ensuring that the axis of the transducer element of the B-scanner, when switched for reception, is situated on the axis of symmetry of the shock wave transducer means at the impingement of the shock wave echo signal.

* * * * *